(12) United States Patent
Baer (10) Patent No.: US 8,958,068 B2
(45) Date of Patent: Feb. 17, 2015

(54) DEVICE FOR DETERMINING THE VOLUME FRACTION OF AT LEAST ONE COMPONENT OF A MULTI-PHASE MEDIUM

(75) Inventor: Christoph Baer, Hattingen (DE)

(73) Assignee: KROHNE Messtechnik GmbH, Duisburg (DE)

( * ) Notice: Subject to any disclaimer, the term of this patent is extended or adjusted under 35 U.S.C. 154(b) by 317 days.

(21) Appl. No.: 13/479,764

(22) Filed: May 24, 2012

(65) Prior Publication Data

US 2012/0300207 A1    Nov. 29, 2012

(30) Foreign Application Priority Data

May 24, 2011    (DE) .......................... 10 2011 102 991

(51) Int. Cl.
*G01J 4/00* (2006.01)
*G01N 22/00* (2006.01)
*G01N 33/22* (2006.01)

(52) U.S. Cl.
CPC .............. *G01N 22/00* (2013.01); *G01N 33/222* (2013.01)
USPC .......................................................... 356/364

(58) Field of Classification Search
CPC ............................... G01N 22/00; G01N 33/222
USPC .............. 356/364, 432, 439, 440; 250/559.09
See application file for complete search history.

(56) References Cited

U.S. PATENT DOCUMENTS

| | | | |
|---|---|---|---|
| 3,283,644 A * | 11/1966 | Saltzman | 250/565 |
| 4,500,835 A * | 2/1985 | Heikkila | 324/631 |
| 4,972,154 A * | 11/1990 | Bechtel et al. | 324/663 |
| 5,619,143 A | 4/1997 | Stevens et al. | |
| 5,650,845 A * | 7/1997 | Kebabian | 356/307 |
| 6,109,097 A | 8/2000 | Conrads et al. | |
| 6,220,077 B1 | 4/2001 | Benichou | |
| 6,661,519 B2 * | 12/2003 | Fukasawa | 356/432 |

(Continued)

FOREIGN PATENT DOCUMENTS

| CA | 2 469 216 A1 | 7/2003 |
|---|---|---|
| JP | 2002-350364 A | 12/2002 |

OTHER PUBLICATIONS

Baer (Conceptual design of a procedure for density monitoring of pulverized fuels in pneumatic conveying systems with microwaves) / Proceedings of the 6th German Microwave Conference / Mar. 14-16, 2011.*

*Primary Examiner* — Michael A Lyons
*Assistant Examiner* — Rufus Phillips
(74) *Attorney, Agent, or Firm* — Roberts Mlotkowski Safran & Cole, P.C.; David S. Safran (57) ABSTRACT

A device for determining the volume fraction of at least one component of a multi-phase medium on the basis of the running time of an electromagnetic desired signal emitted in the multi-phase medium, having at least one emitting device for emitting the desired signal into the multi-phase medium, having at least one receiving device for receiving the desired signal, and having an evaluation device for determining the running time of the desired signal between the emitting device and the receiving device, and at least one polarization device arranged between the emitting device and the receiving device. The desired signal is emitted at least indirectly from the emitting device through the multi-phase medium to the polarization device, the polarization device influences the polarization of the desired signal and the polarization-influenced desired signal is emitted at least indirectly from the polarization device to the receiving device which receives it.

6 Claims, 4 Drawing Sheets

(56) References Cited

U.S. PATENT DOCUMENTS

| | | | |
|---|---|---|---|
| 7,173,706 B2 * | 2/2007 | Wilson et al. | 356/437 |
| 7,712,381 B2 | 5/2010 | Allenberg et al. | |
| 8,332,182 B2 | 12/2012 | Fehrenbach et al. | |
| 8,599,375 B2 * | 12/2013 | Jin | 356/315 |
| 2009/0161105 A1 | 6/2009 | Chen | |

* cited by examiner

DEVICE FOR DETERMINING THE VOLUME FRACTION OF AT LEAST ONE COMPONENT OF A MULTI-PHASE MEDIUM

BACKGROUND OF THE INVENTION

1. Field of the Invention

The invention relates to a device for determining the volume fraction of at least one component of a multi-phase medium on the basis of the running time of an electromagnetic desired signal emitted in the multi-phase medium, having at least one emitting device for emitting the desired signal into the multi-phase medium, having at least one receiving device for receiving the desired signal, and having an evaluation device for determining the running time of the desired signal between the emitting device and the receiving device. Furthermore, the invention relates to a method for operating such a device for determining the volume of at least one component of a multi-phase medium.

2. Description of Related Art

The volume fraction of a component of a multi-phase medium consisting of multiple components can be of interest in technical processes for many different reasons. For example, in the conveying of multi-phase media, the composition, and thus, the density of the conveyed medium is of interest as a rule, since only then can a conclusion be made as to the current flow rate within a process or to which amounts have been conveyed in which composition within a time unit. As an example, pneumatic conveyors are mentioned here, this is a special type of conveying in which gases—for example, air or nitrogen—are used as a conveying medium. On the other hand, the bulk material to be moved is called the conveyed medium. Normally, conveying occurs through tubes or hoses that are sealed against the exterior. A special application is, e.g., the conveying of pulverized coal, which is used for feeding the firing chamber of coal-fired power plants or blast furnaces.

An important process factor in conveying multi-phase media is the mass flow of the conveyed medium, wherein:

$$m\dot{Y} = \frac{\partial m}{\partial t} = \rho \cdot V\dot{Y}$$

The volume flow $V\dot{Y}$ of the conveyed medium is, in turn, described by:

$$V\dot{Y} = \frac{\partial V}{\partial t} = v \cdot A \cdot \zeta,$$

wherein v represents the velocity of the conveyed medium, A the cross section surface of the conveying tube and $\zeta$ the volume fraction of the conveyed medium.

Regardless of the shown example of a pneumatically conveyed bulk material, it is known from the prior to arrive at the volume fraction of a multi-phase medium—for example a dual-phase flow mixture—by measuring the velocity of propagation of electromagnetic waves in the medium, since this velocity of propagation is known to be material-dependent, namely is dependent on the relative permittivity $\in_r$ and the relative permeability $\mu_r$ of a medium:

$$c = \frac{1}{\sqrt{\varepsilon_0 \cdot \varepsilon_r \cdot \mu_0 \cdot \mu_r}} = \frac{c_0}{\sqrt{\varepsilon_r \cdot \mu_r}}$$

When the magnetic characteristics of the individual media of the multi-phase medium are negligible, the velocity of propagation of electromagnetic waves result approximately in $c_0/\sqrt{\in_r}$.

It is known that the effective relative permittivity of a multi-phase medium, in particular a gas-solid mixture, can be determined using suitable mixture formulas, wherein a component of each mixture formula is the relative permittivity of the individual mixed media as well as its volume fraction of the overall volume. When the velocity of propagation of electromagnetic waves is measured within the multi-phase medium, it is possible to arrive at the volume fraction of the conveyed medium using a mentioned mixture formula, however, this will not be discussed in detail here. Details can be found in technical literature (e.g., Sihvola, A: "Mixing Rules with complex Dielectric Coefficients", Subsurface Sensing Technologies and Applications, Vol. 1, No. 4, 2000).

It is further known from the prior art that blank value measurement of the velocity of propagation of electromagnetic waves is initially performed for determining the volume fraction of the components of a dual-phase medium, in which the inner space of the conveying tube is filled with a medium having a known permittivity. A conclusion about the effective relative permittivity of the multi-phase medium can then be made based on the change of the velocity of propagation in comparison to the blank value measurement, for example that the medium can be present as a two-phase flow. With this information, the volume fraction of interest of the conveyed material can be calculated. It is known to use a transmission measurement for this sort of calculation (Baer, C., Musch, T., Gerding, M.: "Conceptual Design of a Procedure for Density Monitoring of Pulverized Fuels in Pneumatic Conveying Systems with Microwaves (8-12 GHz)", Proceeding of the 6th German Microwave Conference, Mar. 14-16, 2011, Darmstadt, Germany).

Here, the volume containing the multi-phase medium is charged with a desired signal emitted by the emitting device, wherein the desired signal passes through the multi-phase medium and is finally received again by a receiving device. If the length of the path is known between the emitting device and the receiving device, the measurement of the running time of the desired signal can lead to the velocity of propagation of the present electromagnetic waves in the form of the desired signal and, from this, finally also to the volume fraction of the components of interest of the multi-phase medium. Interesting information about the transmission behavior of the space filled with the multi-phase medium can be obtained using a network analyzer in a laboratory construction; however, this solution is complex in terms of equipment and thus also expensive. Furthermore, there is the problem that desired signal emitted from the sending device into the multi-phase medium does not arrive at the receiving device in a direct manner through the medium, but rather interference signals are received, which result, for example, from reflections on the walls of a container holding the multi-phase medium or a tube, so that the recognition of the actual desired signal of interest is difficult with the received overall signal.

SUMMARY OF THE INVENTION

A primary object of the present invention is to provide a device for determining the volume fraction of at least one component of a multi-phase medium and a method for operating such a device that makes the determination of the running time of the desired signal within the medium possible with increased accuracy and comparably low technical complexity.

The device according to the invention, in which the above described object is achieved, is initially and essentially wherein at least one polarization device is arranged between the emitting device and the receiving device, the desired signal is emitted at least indirectly from the emitting device through the multi-phase medium to the polarization device, the polarization device influences the desired signal in its polarization and the polarization-influenced desired signal is emitted at least indirectly from the polarization device to the receiving device, wherein the receiving device receives the polarization-influenced desired signal.

The device according to the invention is advantageous in many respects. On the one hand, the polarization device causes the desired signal of interest to be characterized by the produced polarization and thus to be made differentiable among other signals not of interest—interference—which generally makes a better evaluation of the desired signal influenced by polarization and received by the receiving device possible. This is a big advantage over transmission measurement known from the prior art without the intermediary step of polarization influencing of the desired signal emitted in the multi-phase medium. However, it must be provided that the desired signal received by the receiving device can be evaluated in terms of its polarization, i.e., can be vectorially evaluated overall, wherein it is not of importance which method is used for such evaluation; different methods known from the prior art in the fields of time or frequency can be used to recognize a change in the polarization—i.e., a phase shift—and thus to differentiate the desired signals from other signals.

A further advantage of the device according to the invention consists of the emitted desired signal passing through the volume containing the multi-phase medium not just once, but being able to pass through the volume multiple times due to the switching of polarization devices. Thus is it provided according to an advantageous further design of the device according to the invention that the at least one polarization device is arranged in such a manner that the desired signal passes as completely as possible through the volume containing the multi-phase medium, in particular passes completely both on the way from the emitting device to the polarization device as well as on the way from the polarization device to the receiving device. Here, it is by all means possible that both paths are not direct and that an indirect route is taken, for example due to switching of further polarization devices. The volume containing the multi-phase medium can, for example, be limited by a tube through which the multi-phase medium flows. In this case, the desired signal is preferably emitted perpendicular to the direction of flow, wherein the desired signal passes large as possible diameters.

In a design with particularly simple equipment, it is provided that the polarization device is a passive polarization reflector, the emitting device emits the desired signal polarized in a first direction, the passive polarization reflector turns the polarization of the desired signal in a second direction differing from the first direction and further emits the desired signal, and the receiving device receives selectively in the second direction the desired signal polarized in the second direction. The emitting device and the receiving device are aligned in such a manner here that correspondingly long paths result for the desired signal.

In that the receiving device is aligned so that it is particularly sensitive to a desired signal polarized in the second direction—i.e., selectively perceives these—it is guaranteed that other signals not of interest—interference—that result, for example, from interfering reflections of the desired signal on the housing walls are only perceived by the receiving device in a damped manner due to the polarization being generally different.

The above design can be particularly simply structurally implemented in that the emitting device and the receiving device are designed with one common antenna, which serves to emit as well as receive the desired signal. Such an antenna can be designed, for example, as a waveguide or horn antenna, wherein the emitted desired signal is then normally linearly polarized. In this case, the emitting of the desired signal in a first polarization direction and the receiving in a second polarization direction different than the first is implemented in that a waveguide is designed in the antenna with different paths for the emitting device, on the one hand, and the receiving device, on the other hand, wherein the orientation of these paths correspond to the desired polarization directions of the emitted and received desired signal. The passive polarization reflector can, for example, be a cross polarization reflector that causes a 90° turn in the polarization direction, so that the paths for the emitting device, on the one hand, and the receiving device, on the other hand, are offset to one another by 90°.

A further preferred design of the invention differs from the above-mentioned designs in that the polarization device is not a passive device, but rather is designed as an active polarization device, the emitting device emits the desired signal polarized in a first direction, the active polarization device turns and emits the desired signal in a second direction and the receiving device receives the desired signal polarized in the second direction and the evaluating device vectorially evaluates the received complete signal so that the desired signal polarized in the second direction can be differentiated from other parts of the received complete signal, in particular, from interference signals. In this design, the desired signal of interest is also characterized by polarization and is made differentiable from interference radiation not having this polarization. Furthermore, the volume filled with the multi-phase medium is passed through twice, so that a double length as opposed to the one-way transmission measurement is made available and, thus, the relative measuring error is smaller. Vectorial evaluation of the received complete signal—as described above—means that the received signal is evaluated according to amount and phase, so that different polarized parts can be differentiated from one another.

Passive and active polarization devices can be positively combined with one another, so that a further preferred design of the device according to the invention is wherein a first, passive polarization device and a second, active polarization device are provided, the emitting device and the receiving device have a first common polarization orientation and the second, active polarization device has a second polarization orientation differing from the first polarization orientation. Such a device is designed in such a manner that the emitting device initially emits the desired signal polarized in the first polarization orientation and through the medium and the first, i.e., passive polarization device turns the desired signal in the second polarization orientation and emits it through the medium. This desired signal vibrating in the second polarization direction can only influence the receiving device in a small way, even when it is reflected in the direction of the receiving device since the receiving device is not sensitive by definition to this polarization direction.

The device is then further designed so that the second, active polarization device turns the desired signal and emits it, in turn, through the medium and the first, passive polarization device turns this desired signal, in turn, in the first polarization orientation and further emits it through the medium, whereupon the receiving device receives the desired signal and the evaluating device vectorially evaluates the received complete signal so that the desired signal polarized in the second direction can be differentiated from other parts of the received complete signal. In a concrete example, it is also possible that the emitting device emits a vertically polarized desired signal that is turned 90° by the first, passive polarization device, thus, is practically not able to be received by the receiving device; the second, active polarization device then turns the desired signal, for example, 180°—reflection factor 1—, the signal is then emitted to the first, passive polarization device and turned another 90° there and is thus receivable again for the receiving device. In such an arrangement, the desired signal passes through the volume containing the medium four times, which leads to a corresponding reduction of the measuring error. The advantage of characterizing the desired signal of interest as opposed to the interference signal, which is not of interest and is to be suppressed, is further achieved in this manner.

Furthermore, the invention relates to a method for operating an above-mentioned device for determining the volume fraction of at least one component of a multi-phase medium on the basis of the running time of an electromagnetic desired signal emitted in the multi-phase medium, wherein the method only relates to such devices that have at least one active polarization device, i.e., such a polarization device that can be pre-set whether it carries out a certain polarization or does not carry out a polarization, or such a polarization device in which arbitrary polarization influences can be pre-set, which is not just turned on and off.

In the method according to the invention a polarization influence is set during a first measurement by the active polarization device and a first received signal is detected by the receiving device. Then, a second polarization influence different than the first polarization influence is set during a second measurement by the active polarization device and a second received signal is detected. According to this, there are two received signals with differently polarized desired signals. Then, the first received signal and the second received signal are superimposed in such a manner that interference signals contained in the first received signal and the second received signal are nullified, in particular desired signals contained in the first received signal and in the second received signals are added together. This can be easily imagined, for example, in a first measurement, in which the active polarization device is deactivated, i.e., the first polarization influencing is implemented as a non-influencing factor, wherein the active polarization device is set in the second measurement in which a negative reflection factor is implemented, i.e., a phase shift of the desired signal of 180° is implemented. When the part of the received complete signal that shows this phase shift, which therefore comes from the desired signal of interest, is associated with a negative sign and the first received signal and the second received signal influenced in this manner are subsequently subtracted from one another, the interference signals contained in the received signals are practically nullified—provided that they have the same structure, because they come from solid reflection surfaces—while desired signals having different signs are added together, which simplifies the recognition of the desired signal overall, and thus, the determination of the signal running time.

In detail, there are a number of possibilities for designing and further developing the device according to the invention and the method according to the invention. As such, reference should be made to the following detailed description of preferred embodiments in conjunction with the accompanying drawings.

DETAILED DESCRIPTION OF THE INVENTION

Figure 1:
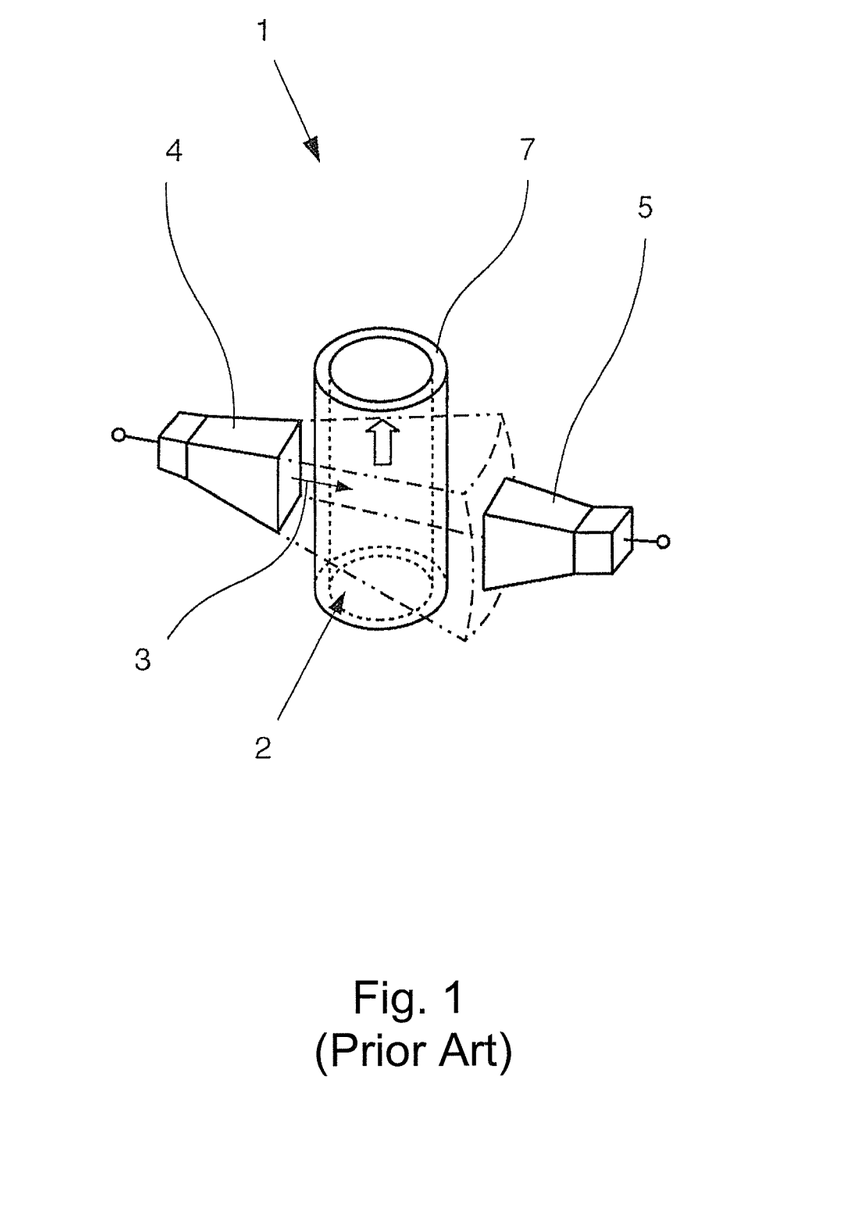
FIG. 1 is a perspective view of a device for determining the volume fraction of at least one component of a multi-phase medium according to the prior art.

A device 1 is shown in FIG. 1 for determining the volume fraction of at least one component of a multi-phase medium 2 on the basis of the running time of an electromagnetic desired signal 3 emitted in the multi-phase medium 2, having an emitting device 4 for emitting the desired signal 3 into the multi-phase medium 2, having a receiving device 5 for receiving the desired signal 3 and having an evaluating device, not shown here, and identified with the reference number 6 in other figures for determining the running time of the desired signal 3 between the emitting device 4 and the receiving device 5.

In the present case, the multi-phase medium 2 is lead in a tube 7, wherein the medium 2 moves in the direction given by the arrow. In the prior art, the desired signal 3 emitted by the emitting device 4 and the desired signal 3 received by the receiving device 5 are lead to a network analyzer via high frequency lines, from which conclusions can be drawn about the transmission behavior of the entire path and thus also about the running time of the desired signal 3 between the emitting device 4 and the receiving device 5. It can be a problem that the complete signal received by the receiving device 5 not only contains the desired signal 3 of interest, but also interference signals, as the differentiating of desired signals and interference signals requires a great effort, is partly impossible, is complex in terms of equipment and cannot be carried out in a process in industrial practice.

Figure 2:
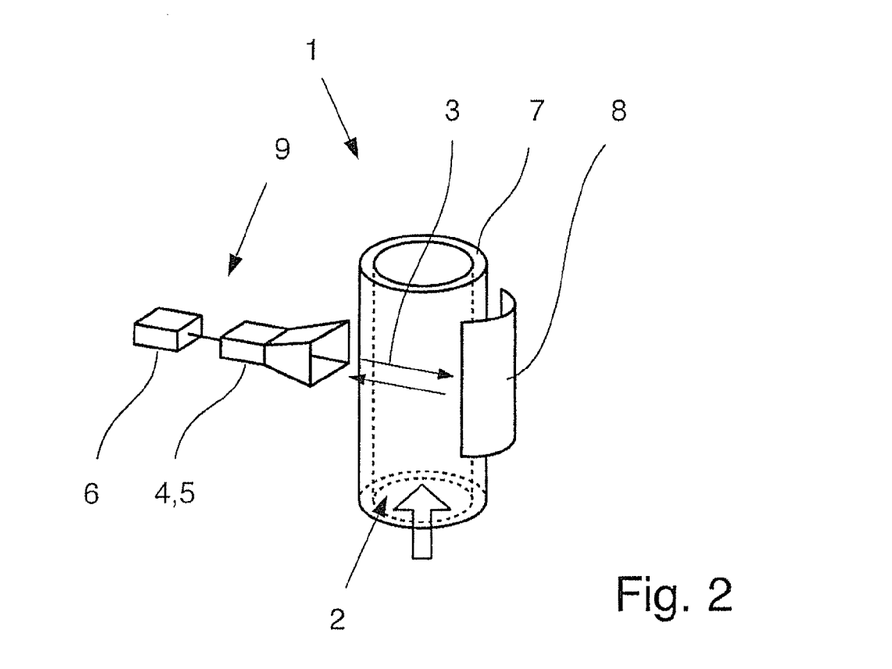
FIG. 2 is a perspective view of a device according to the invention shown schematically having two measuring paths and a passive polarization device.
Figure 6:
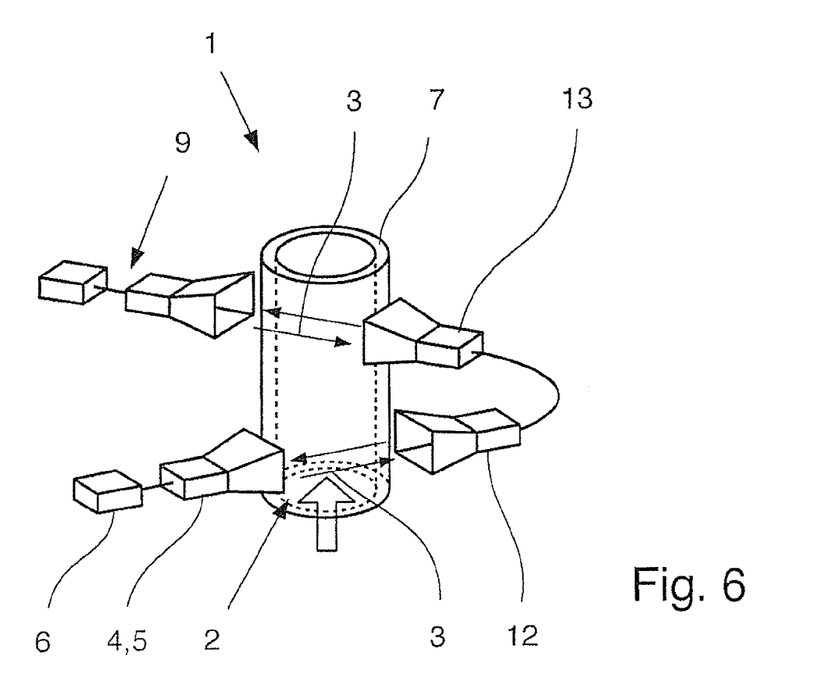
FIG. 6 is a perspective view of yet another embodiment of a device according to the invention with four measuring paths.

Both of the embodiments of FIGS. 2 & 6 share the feature that at least one polarization device 8, 9 is arranged between the emitting device 4 and the receiving device 5, the desired signal 3 is emitted from the emitting device 4 through the multi-phase medium 2 to the polarization device 8, 9, the polarization device 8, 9 influencing the polarization of the desired signal 3 and emits the polarization-influenced desired signal 3 through the medium from the polarization device 8, 9 to the receiving device 5. The receiving device 5 receives the polarization-influenced and, thus, individualized desired signal 3. Before the desired signal 3 is received by the receiving device, the desired signal 3 is made differentiable from other signals contained in the complete signal, i.e., interference signals, by its polarization.

As can be seen in all of FIGS. 2-6, the polarization device 8, or the polarization device 9 or the polarization devices 8, 9 are arranged so that the desired signal 3 passes as completely as possible through the tube 7 containing the multi-phase medium 2, on the way from the emitting device 4 to the polarization device 8, 9 as well as on the way from the polarization device 8, 9 to the receiving device 5. The desired signal 3 thus passes through the volume containing the multi-phase medium 2 at least twice, or even more often, in the device according to the invention, which accordingly reduces measuring error. The desired signal 3 is, in particular, emitted in such a manner that is runs perpendicular to the direction of flow.

In the embodiment according to FIG. 2, the polarization device 8 is a passive polarization reflector. The emitting device 4 emits the desired signal 3 polarized in a first direction, the passive polarization reflector 8 turns the polarization of the desired signal 3 in a second direction that is different from the first direction, presently, namely by 90°, and further emits the desired signal 3. The receiving device 5 is in a structural unit with the emitting device 4 and is designed in such a manner that it selectively, in the second direction, receives the desired signal that has been polarized in the second direction. The different polarization directions of the emitting device 4 and the receiving device 5 are implemented in the illustrated embodiment in such a manner that different paths for the emitting device 4, on the one hand, and the receiving device 5, on the other hand, are designed in a waveguide of the illustrated antenna, corresponding to the polarization directions of the emitted and received desired signal 3 that are at 90° relative to one another. Presently, the passive polarization reflector 8 is a cross polarization reflector.

Figure 3:
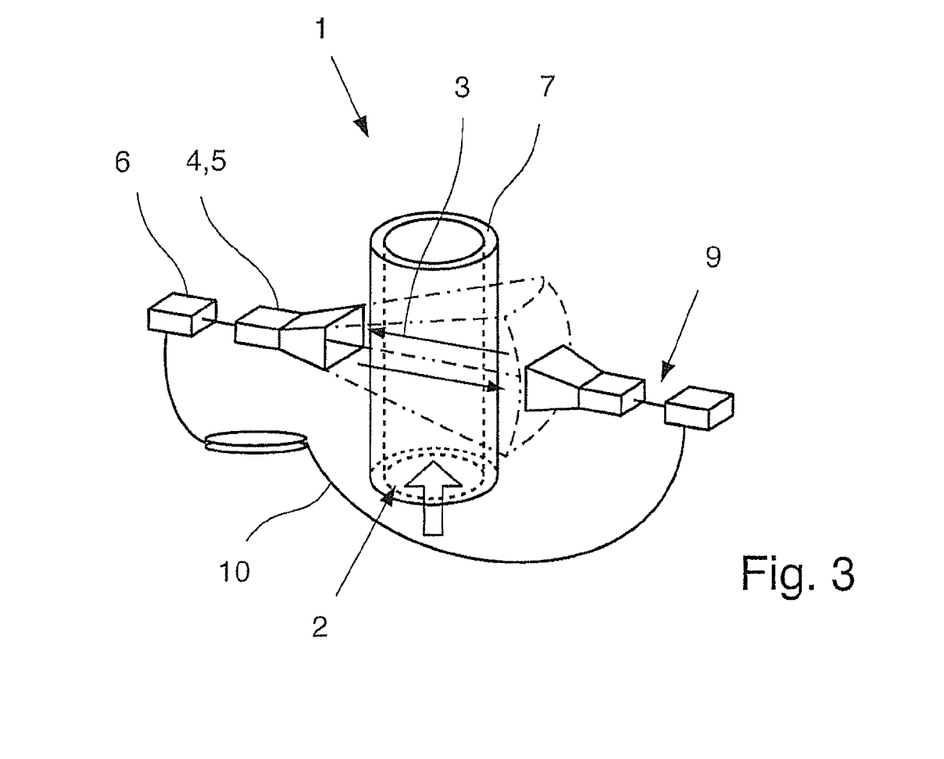
FIG. 3 is a perspective view of a further embodiment of a device according to the invention having an active polarization device and two measuring paths.

In the embodiment shown in FIG. 3, the polarization device 9 is implemented by an active polarization device 9, that can be pre-set at a certain polarization or a certain polarization change or can be turned on and off in respect to polarization influencing. For this purpose, the polarization device 9 is connected to the evaluating device 6 with a low frequency cable 10, which takes on this task of control. The active polarization device 9 is implemented here by a modulator with switchable reflection coefficients.

The emitting device 4 emits the desired signal 3 polarized in a first direction. The active polarization device 9 then turns the desired signal 3 in a second direction and further emits the desired signal 3, namely back in the direction of the receiving device 5, which receives the desired signal 3 polarized in the second direction. The evaluating unit 6 subsequently vectorially evaluates the received complete signal, so that the desired signal 3, polarized in the second direction, is differentiable from other parts of the received complete signal, in particular, is differentiable from the received interference signal. Here, the desired signal 3 also passes through the volume in the form of a tube 7 filled with the multi-phase medium 2 twice. The switching of the active polarization device 9 with the low frequency cable 10 is simple and inexpensive, since procedures critical in terms of time in respect to running time of the desired signal 3 do not have to be taken into consideration.

Figure 4:
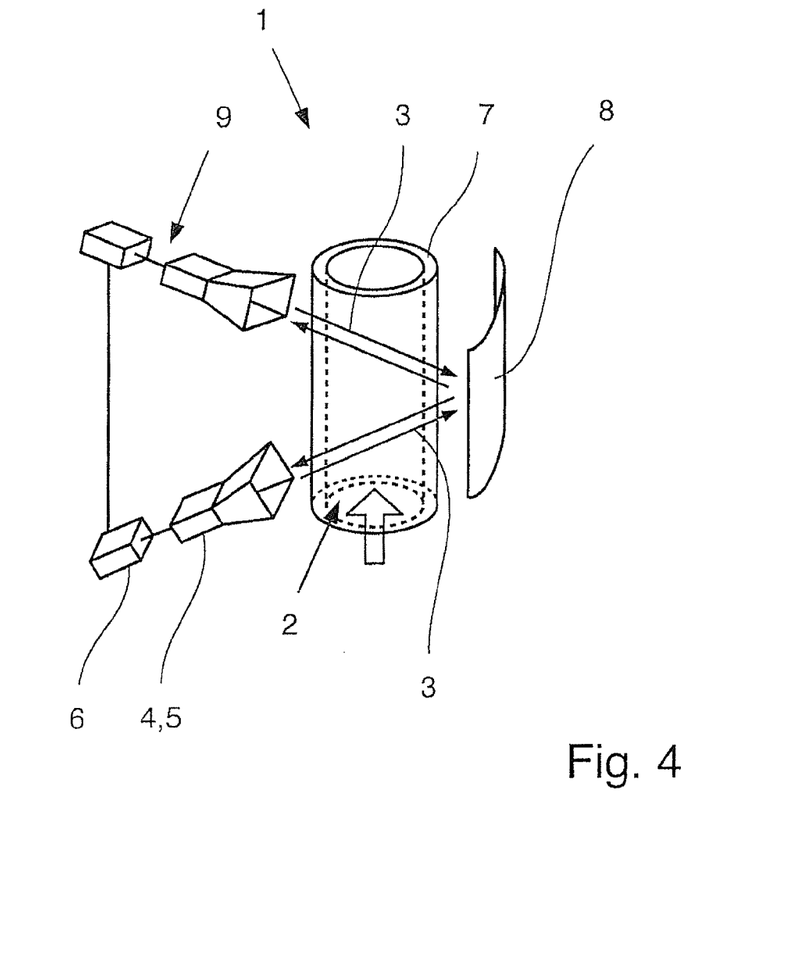
FIG. 4 is a perspective view of a another embodiment of a device according to the invention having a passive polarization device and an active polarization device and four measuring paths, in total.

In the embodiment according to FIG. 4, a first, passive polarization device 8 as well as a second, active polarization device 9 are provided. The emitting device 4 and the receiving device 5 have a first polarization direction, the second, active polarization device 9 has a second polarization direction that differs from the first polarization direction; presently, the polarization directions are turned 90° to one another. The emitting device 4 emits the desired signal 3 into the medium 2 polarized in the first polarization direction. The first, passive polarization device 8 turns the desired signal 3 90° into the second polarization direction and emits the polarization-influenced desired signal 3 further in this manner into the medium 2. This emitted desired signal 3 cannot disrupt the receiving device 5, since the receiving device 5 is not sensitive to this polarization direction. The second, active polarization device 9 is designed as a modulator and causes a turn in the phase of the received desired signal 3 of 180° and a subsequent further emission of the desired signal 3 through the medium 2. The polarization-influenced desired signal 3 cannot yet be received by the receiving device 5 and does not disturb the receiving device 5. The desired signal 3 is finally turned another 90° into the first polarization direction by the first, passive polarization device and is emitted another time from there into the medium 2, and subsequently, can be received by the receiving device 5. The evaluating unit 6, in turn, vectorially evaluates the received complete signal with the goal that the desired signal 3, polarized in the second direction, can be differentiated from other parts of the received complete signal and is differentiated. In this solution, the desired signal passes through the medium 2 four times with the described positive effect on the measuring accuracy.

Figure 5:
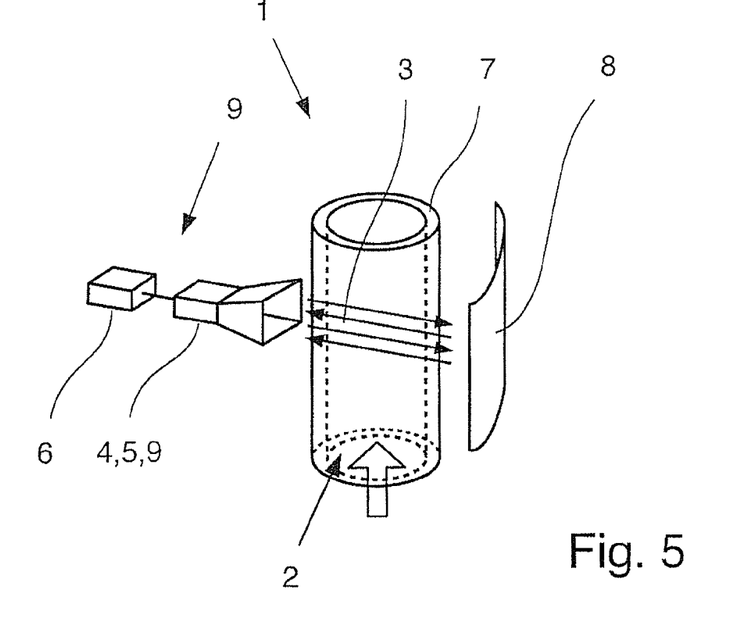
FIG. 5 is a perspective view of a further embodiment of a device according to the invention, wherein the emitting device, the receiving device and the polarization device subside in one device.

The embodiment according to FIG. 5 is functionally similar to the embodiment according to FIG. 4, wherein the emitting device 4, the receiving device 5 and the second, active polarization device 9 are designed with a common antenna. The emitting device 4 and the receiving device 5 have a first, common polarization direction and the second, active polarization device 9 has a second polarization direction, differing from the first polarization direction. The functional principle is similar to the embodiment according to FIG. 4; however, the construction is considerably more compact due to the summarization of equipment.

The embodiment according to FIG. 6 is functionally very similar to the embodiment according to FIG. 3, wherein the measuring path is extended by the phase location and the polarization of non-influencing antennae 12, 13. The measuring paths between the emitting device 4 or the receiving device 5 and the antenna 12, on the one hand, as well as between the antenna 13 and the second, active polarization device 9, on the other hand, are turned 90° relative to one another—intended rotation axis of the tube 7—and are spaced from one another in the flow direction of the tube. It is of advantage here that an averaging over two different tube cross sections occurs using the geometrical separation of the pair of antennae 4, 5, & 12, on the one hand, and antennae 13 and 9, on the other hand, which also increases measuring accuracy.

In the illustrated embodiments according to FIGS. 3 to 6, which have an active polarization device 9, the evaluating device 6 is designed in such a manner that the method described subsequently for operating the device can be carried out. According to this, a first polarization influence is set by the active polarization device 9 during a first measurement, which presently comprises the desired signal 3 simply being reflected. The receiving device 5 detects the first received signal. During the second measurement, the active polarization device 9 emits a second polarization influence, different than the first polarization influence, presently a negative reflection factor is set and a second received signal is detected by the receiving device 5. The evaluating device 6 calculates the first, received signal and the second, received signal in such a manner that the interference signals contained in the first, received signal and in the second, received signal—at least for the most part, insofar as they are similar—nullify one another, through which the desired signal 3 can be considerably more reliably detected in the complete signal and leads to the running time measurement of the desired signal improving in quality.

Specifically, a positive reflection coefficient is set during the first measurement by the second polarization device 9 and a negative reflection coefficient is set during the second measurement by the second polarization device 9, wherein the phase switch of the desired signal is identified in the second measurement and is taken into consideration in terms of sign in the second, received signal. Thus, it is possible that the interference signals are nullified by superimposing both received signals over one another and adding the desired signals.

What is claimed is:

1. Device for determining the volume fraction of at least one component of a multi-phase medium on the basis of the running time of an electromagnetic desired signal emitted in the multi-phase medium, comprising:
at least one emitting device for emitting a desired signal into the multi-phase medium,
at least one receiving device for receiving the desired signal, and
an evaluation device for determining the running time of the desired signal between the emitting device and the receiving device, and
at least one polarization device arranged in a path of the desired signal between the emitting device and the receiving device, the polarization device being adapted to influence the polarization of the desired signal emitted by the at least one emitting device and passing through the multi-phase medium and for at least indirectly directing the polarization-influence desired signal to the receiving device,
wherein the at least one polarization device comprises a passive polarization reflector, wherein the emitting device is adapted to emit the desired signal with a polarization in a first direction, wherein the passive polarization reflector is adapted to cause the polarization-influenced desired signal to have a polarization in a second direction which is different from the first direction, and wherein the receiving device being adapted to selectively receive the polarization-influenced desired signal polarized in the second direction, and wherein the emitting device and the receiving device share a common waveguide antenna having different paths for the emitting device and the receiving device corresponding to the polarization direction of the emitted and received signals.

2. Device according to claim 1, wherein the at least one polarization device is arranged in such a manner that the desired signal passes as completely as possible through the volume containing the multi-phase medium both on the way from the emitting device to the polarization device as well as on the way from the polarization device to the receiving device.

3. Device according to claim 1, wherein the at least one polarization device comprises an active polarization device, and wherein the evaluating device is adapted to vectorially evaluate the received signal so that the signal polarized in the second direction can be differentiated from other fractions of the received signal.

4. Device according to claim 3, wherein the active polarization device comprises a modulator for implementing variable reflection coefficients.

5. Device for determining the volume fraction of at least one component of a multi-phase medium on the basis of the running time of an electromagnetic desired signal emitted in the multi-phase medium, comprising:
at least one emitting device for emitting a desired signal into the multi-phase medium,
at least one receiving device for receiving the desired signal, and
an evaluation device for determining the running time of the desired signal between the emitting device and the receiving device, and
at least one polarization device arranged in a path of the desired signal between the emitting device and the receiving device, the polarization device being adapted to influence the polarization of the desired signal emitted by the at least one emitting device and passing through the multi-phase medium and for at least indirectly directing the polarization-influence desired signal to the receiving device
wherein at least one polarization device comprises a first, passive polarization device and a second, active polarization device, wherein the emitting device and the receiving device have a first polarization orientation, wherein the second, active polarization device has a second polarization orientation that is different from the first polarization orientation, wherein the emitting device is adapted to emit the desired signal polarized in the first polarization orientation and through the medium, wherein the first, passive polarization device is adapted to turn the desired signal in the second polarization orientation and emit it through the medium, wherein the second, active polarization device is adapted to turn the desired signal and emit it through the medium to the receiving device and where the evaluating device is adapted to vectorially evaluate the received signal and differentiate the signal polarized in the second direction from other fractions of the received signal, wherein the emitting device, the receiving device and the second, active polarization device share a common antenna, and wherein the emitting device and the receiving device have a first polarization orientation and the second, active polarization device has a second polarization orientation that is different from the first polarization orientation.

6. Device according to claim 5, wherein the common antenna is a waveguide antenna having two different paths for the emitting device and the receiving device and for the second, active polarization device one path corresponding to the polarization orientation of the desired signal emitted by the emitting device and received by the receiving device, and the other path corresponding to the polarization orientation of the signal emitted and received by the second, active polarization device.

* * * * *